US006860980B2

(12) United States Patent
Locascio et al.

(10) Patent No.: US 6,860,980 B2
(45) Date of Patent: Mar. 1, 2005

(54) POLYELECTROLYTE DERIVATIZATION OF MICROFLUIDIC DEVICES

(75) Inventors: Laurie E. Locascio, North Potomac, MD (US); Susan L. R. Barker, Charlottesville, VA (US); David Ross, Germantown, MD (US); Michael J. Tarlov, Bethesda, MD (US)

(73) Assignee: The United States of America as represented by the Secretary of Commerce, Washington, DC (US)

( * ) Notice: Subject to any disclaimer, the term of this patent is extended or adjusted under 35 U.S.C. 154(b) by 596 days.

(21) Appl. No.: 09/881,123

(22) Filed: Jun. 15, 2001

(65) Prior Publication Data

US 2002/0053514 A1 May 9, 2002

Related U.S. Application Data

(60) Provisional application No. 60/232,951, filed on Sep. 15, 2000.

(51) Int. Cl.[7] ............................................. G01N 27/447
(52) U.S. Cl. .................... 204/601; 204/600; 436/516
(58) Field of Search ................................ 204/600, 601; 436/516

(56) References Cited

U.S. PATENT DOCUMENTS

| | | | |
|---|---|---|---|
| 5,208,111 A | | 5/1993 | Decher et al. |
| 5,770,029 A | * | 6/1998 | Nelson et al. ............... 204/604 |
| 5,858,188 A | * | 1/1999 | Soane et al. ................. 204/454 |
| 6,020,175 A | | 2/2000 | Onda et al. |
| 6,402,918 B1 | | 6/2002 | Schlenoff et al. |

OTHER PUBLICATIONS

Katayama et al. "Stable Cationic Capillary Coating with Successive Multiple Ionic Polymer Layers for Capillary Electrophoresis", Anal. Chem., 1998, v. 70, pp, 5272–5277.*

Tronin et al. "Ellipsometry and x–ray reflectometry characterization of self–assembly process of polystyrene sulfonate and polyallylamine", Colloid and Polymer Science (1994), 272(10), 1317–21 (Abstract).*

Stroock et al. "Patterning Electro–osmotic Flow with Patterned Surface Charge", Phys. Rev. Lett., Apr. 10, 2000, v. 84, No. 15, pp. 3314–3317.*

Caruso et al. "Protein Multilayer Formatin on Colloids through a Stepwise Self–Assembly Technique", J. Am.Chem. Soc., 1999, v. 121, pp. 6039–6046.*

Barker et al. "Control of Flow Direction in Microfluidic Devices with Polyelectrolyte Multilayers", Anal. Chem., 2000, v. 72, pp. 592505929.*

Ladam et al. "Protein Interactions with Polyelectrolyte Multilayers: . . . ", Biomacromolecules, 2000, v. 1, pp. 674–687.*

Pfohl et al. "Controlled Modification of Microstructures Silicon Surfaces for Confinement of Biological Macromolecules and Liquid Crystals", Langmuir, 2001, v. 17, pp. 5343–5351.*

(List continued on next page.)

*Primary Examiner*—Yelena G. Gakh
(74) *Attorney, Agent, or Firm*—Stites & Harbison PLLC; Ross F. Hunt, Jr.

(57) ABSTRACT

A microchannel device is provided with a plastic substrate having a microchannel formed therein. Polyelectrolyte multilayers are disposed along selected surfaces of the microchannel. The polyelectrolyte layers comprise alternating net positively charged layers and net negatively charged layers. A microchannel lid has a surface facing the microchannel. In making the microchannel device, selected surfaces of the microchannel are alternatively exposed to solutions comprising positively charged polyelectrolytes and negatively charged polyelectrolytes to form the desired number of polyelectrolyte layers.

42 Claims, 4 Drawing Sheets

OTHER PUBLICATIONS

Xu et al.; "Room–temperature Imprinting Method for Plastic Microchannel Fabrication"; *Analytical Chemistry*, vol. 72, No. 8, Apr. 15, 2000; pp. 1930–1933.

Martynova et al.; "Fabrication of Plastic Microfluid Channels by Imprinting Methods"; *Analytical Chemistry*, vol. 60, No. 23, Dec. 1, 1997; pp. 4783–4789.

* cited by examiner

POLYELECTROLYTE DERIVATIZATION OF MICROFLUIDIC DEVICES

CROSS-REFERENCE TO RELATED APPLICATIONS

This application claims benefit of the filing date of copending Provisional Patent Application No. 60/232,951, filed on Sep. 15, 2000, the disclosure of which is herein incorporated by reference.

STATEMENT REGARDING FEDERALLY SPONSORED RESEARCH

This invention was made by employees of the United States Government and may be manufactured and used by or for the Government for governmental purposes without the payment of any royalties.

BACKGROUND OF THE INVENTION

1. Field of the Invention

The present invention relates to a microchannel device, and in particular, a microchannel device comprising a microchannel having microchannel wall surfaces with polyelectrolyte multilayers of alternate charge formed thereon.

2. Background of the Invention

In the past few years, there has been an increasing interest in the field now generally known as microfluidics. An important challenge in developing the first generation of microanalytical systems is in the successful design and fabrication of microcapillary channels and networks formed thereof, collectively referred to as microchannels. The microchannels may be composed of intersecting subchannels thereby forming a plurality of microchannel arms. These microchannels may be ultimately incorporated into self-contained analytical systems with detection and processing elements for use to perform chemical or biochemical measurements. Fluid transport in the microchannels may be accomplished using electroosmotic, thermal, or mechanical pumping. Chemical selectivity may be achieved using a number of analytical techniques including electrophoresis or chromatography (adsorption, affinity, or ion exchange).

Most prototype devices to date have been fabricated in glass or silica- or silicon-based substrates. Fine lithographic processing techniques are used to produce microchannels in the surface of a planar substrate that are then covered with a plate of similar material or different material thereby forming a lid over the microchannel.

For silica- and silicon-based devices, the most common methods for sealing the lid over the microchannels include high-temperature annealing, anodic bonding and wafer bonding depending upon the substrate material. Although successful prototype devices have been prepared using silica- or silicon-based substrates, the associated fabrication techniques of microchannel fabrication and sealing are generally difficult and/or expensive to implement.

Due to the aforementioned limitations associated with silica and silicon-based substrates, other materials such as polymers have been proposed as alternate substrates for the fabrication of microfluidic devices. Interest in using polymer substrates, such as plastics, for the production of microanalytical systems, is driven by the fact that these materials are less expensive and easier to manipulate than silicon or silica-based substrates. Further, plastics lend themselves readily to casting, molding, laser ablation, and machine operations. A wide variety of low-cost polymer materials enable selection for thermal and chemical resistance, molding temperature and surface derivatization properties.

A major obstacle in implementing microchannels fabricated in plastic substrates is that plastic surface chemical functionalities are not well characterized as compared to glass or silicon substrates. The surface can vary significantly from one plastic to another, and similar plastics can vary among commercial vendors. One such functionality is surface charge and surface charge density.

Surface charge and surface charge density is important in microfluidics for a number of reasons. Electroosmotic flow (EOF) is commonly used to move fluids through microchannels. This phenomenon is driven by charge (ionic) groups on the microchannel walls when an electric field is applied along the length of the microchannel. The direction and rate of EOF is determined by the charge and charge density, respectively, on the walls of the microchannel. Therefore, differences in microchannel surface chemistry can have a dramatic effect on flow rates and separations in devices utilizing EOF. For example, microchannels fabricated in various plastic substrates can exhibit dramatically different EOF mobilities (e.g., faster or slower flow rates). Thus, development of methods for controlling microchannel surface chemistry is critical for controlling flow rates and flow direction when EOF is employed to manipulate fluid flow.

Many common polymeric surfaces are either uncharged and extremely hydrophobic or negatively charged; however, biocompatible surfaces are generally hydrophilic with a net positively-charged surface. Therefore, for many applications of microfluidic devices in biotechnology, it would be desirable to identify coatings that could alter polymeric surfaces to make them hydrophilic and positively charged to minimize nonspecific adsorption of biological species.

Finally, many polymer-based microchannels require priming of the surfaces of the microchannel before use, i.e. the introduction of a fluid sample. Because several common polymers are hydrophobic in nature, priming of the microchannel may involve rinsing the microchannel with alcohol to first wet the surface, then filling the microchannel with water, and finally filling the microchannel with buffer solution. Air bubbles are often trapped in the primed polymeric microchannel when introducing a fluid sample, even if great care is taken to wet the surface prior to filling with buffer. These air bubbles may interfere with the analytical systems in which the microchannel is deployed. Therefore, coatings that reduce the hydrophobicity of polymeric microchannels are desirable.

BRIEF SUMMARY OF THE INVENTION

In accordance with the present invention, polyelectrolyte multilayers are used to alter the surface of microchannels fabricated in polymer-based substrates (e.g., either plastics or pure polymers). In addition, the polyelectrolyte multilayers (PEMs) can be used to control the direction of flow of a fluid through the microchannels in a microfluidic device. Further, complex flow patterns, including flow in opposite directions in the same microchannel, can be generated in a microchannel with opposing surfaces having opposite charges.

According to one aspect of the present invention, a microchannel device comprises a plastic substrate having a microchannel formed therein. Polyelectrolyte layers comprise alternating layers of at least one net positively charged layer or negatively charged layer. The polyelectrolyte multilayers are disposed along at least a portion of a microchannel surface. A lid is disposed over the microchannel with a lid surface facing the microchannel.

In accordance with another aspect of the present invention, a method is provided for manufacturing a microchannel device comprising the steps of providing a plastic substrate with a microchannel formed therein. The microchannel has one or more spatial dimensions in the micrometer-size range. When the polymer surface has a net negative charge, selected surfaces of the microchannel are exposed to a first solution comprising positively charged polyelectrolytes. If positively charged, the first solution is negatively charged polyelectrolytes. In the first case, the selected surfaces of the microchannel are exposed to a second solution comprising negatively charged polyelectrolytes. The steps of exposing the selected surfaces of the microchannel to the first solution and exposing the selected surfaces of the microchannel to the second solution are repeated, alternatively, as necessary, to form a desired number of polyelectrolyte layers on the selected surfaces.

The present invention, according to yet another aspect thereof, concerns a microchannel device comprising a plastic substrate having a microchannel formed therein. The microchannel has a first microchannel wall portion and a second microchannel wall portion. A polyelectrolyte layer is disposed as an outermost surface on the first microchannel wall portion and a second polyelectrolyte layer of opposite charge is exposed as an outermost surface on the second microchannel wall portion. A lid is disposed over the microchannel and has a lid surface facing the microchannel. The lid may be applied before or after deposition of the polyelectrolytes.

According to another aspect of the present invention, a method of manufacturing a microchannel device comprises the steps of providing a plastic substrate with a microchannel formed therein. At least one polyelectrolyte layer is formed on selected surfaces of the microchannel by exposing a selected portion of a first microchannel wall surface and a selected portion of the second microchannel wall surface of the microchannel to a first solution comprising first charge polyelectrolytes. The selected portion of the first microchannel wall surface is selectively exposed to a second solution comprising second charged polyelectrolytes. The second charged polyelectrolytes have a charge opposite a charge of the first polyelectrolytes.

One key feature of the present invention relates to altering the charge on the surfaces of a microchannel via PEM derivatization. Through PEM derivatization of a variety of different substrate materials which have different native EOF mobilities, similar EOF rates now can be achieved in microchannels formed in a variety of different materials. Thus, the present invention provides the advantage of the use of different materials while maintaining a similar EOF rate which was not easily achieved using underivatized (i.e., native) plastic materials.

Another feature of the use of PEMs according to the present invention is to create a microchannel with positively charged microchannel surfaces and negatively charged microchannel surfaces. Since the direction of the EOF fluid flow is determined by surface charge on the walls of a microchannel, PEMs can be used to control the direction in which an EOF fluid moves in a microchannel of a microfluidic device.

Still another feature of the present invention relates to providing a microchannel that allows flow of a fluid in opposite directions in the same microchannel. This may be achieved by derivatization of opposite sides of a plastic microchannel with oppositely charged polyelectrolytes to achieve side-by-side opposite flows. Alternatively, top-bottom opposite flows may be achieved by having a positively derivatized plastic substrate with a negatively charged lid or visa versa.

A further feature of relatively complex flow patterns may be provided by implementing the present invention to selectively apply various charged layers to selected surfaces, or portions of a microchannel, in a microchannel device. For example, the present invention can be implemented to produce a microchannel comprising different arms having surfaces of opposite charges.

Another feature is to increase biocompatibility of plastic microchannels in a generic way using PEMs.

A further feature of the present invention relates to enhanced wettability of microchannels derivatized using PEMs. As a result, priming the microchannel before introducing a fluid sample becomes unnecessary. Further, air bubbles are less likely to get pinned on the microchannel surface of the derivatized microchannels.

Yet another feature of the PEMs coated microchannel walls of the present invention is the ability to attach other molecules to the microchannel wall. Such immobilization allows for attachment or entrapment of molecules such as proteins, antibodies and DNA to the walls of a microchannel formed in a variety of substrates.

Further features and advantages of the present invention will be set forth in, or apparent from, the detailed description of preferred embodiments thereof which follows.

DETAILED DESCRIPTION OF THE INVENTION

Figure 1A:
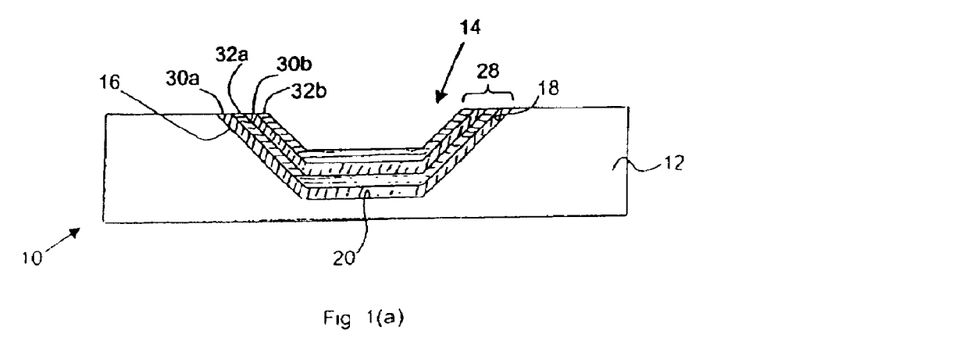
FIG. 1(a) is a cross-sectional view of a microfluidic device having a PEMs derivatized multichannel according to the present invention.
Figure 1B:
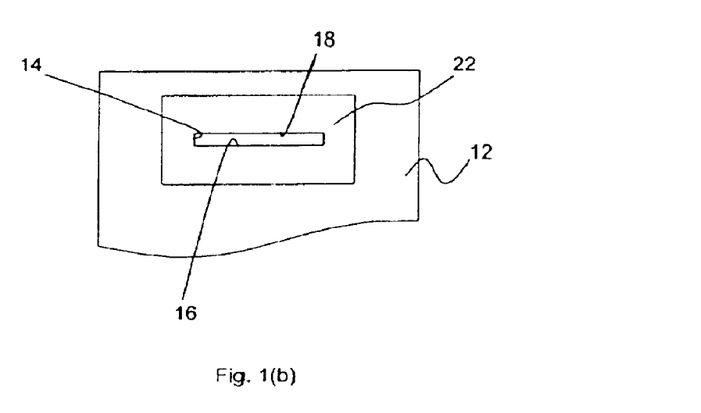
FIG. 1(b) is a top view of the microchannel device of FIG. 1(a)

Referring now to the figures, and in particular, to FIGS. 1(a) and 1(b), microfluidic device 10 comprises a plastic substrate 12. The plastic substrate 12 may be composed of any suitable plastic or polymer material which includes but is not limited to polystyrene (PS), poly(ethylene terephthalate glycol) (PETG), poly(methyl methacrylate) (PMMA), and polycarbonate (PC).

A microchannel 14 formed in substrate 12 has a trapezoidal cross-section defined by slanted sidewalls 16, 18. Alternatively, the side wall surfaces of the microchannel 14 could be substantially perpendicular to a bottom surface 20. Alternatively, the microchannel could have sloped side walls, straight side walls without a well defined floor (V groove) or curved, semicircular side walls forming a "U-shaped" groove, or any other configuration with a channel that has one or more spatial dimensions in the micrometer size range. The depth of microchannel 14 is between 0.05 and 1000 µm and optimally between 1 and 100 µm. The width of microchannel 14 is between 0.05 and 5000 µm and optimally between 1 and 1000 µm.

Using standard microchannel formation techniques known in the art, a silicon template, fabricated by photolithography, can be used to imprint microchannel 14. Further details on the imprinting process may be made by reference to Xu, J. et al., *Anal. Chem.* 2000, 72, 1930–1933, herein incorporated by reference. Alternatively, hot imprinting can be used to form microchannel 14. Microchannels can also be formed by other common techniques including but not limited to laser ablation, X-ray lithography, soft lithography, or injection molding.

The microchannel 14 is sealed using a lid 22 (FIG. 1(*b*)). For clarity, lid 22 is not depicted in FIG. 1(*a*). In a preferred embodiment, lid 22 comprises a film which seals microchannel 14.

Polyelectrolyte multilayers or PEMs 28 are disposed on the inner surfaces of the microchannel 14. In the case of a trapezoidal channel, sidewalls 16, 18 and bottom surface 20 of microchannel 14 can be coated, as well as the lid made of the same material or a different material. In the case where the lid is not coated, the lid retains the native charge of the polymer substrate. In the case where the substrate is negatively charged, the first PEMs layer is positive. PEMs 28 comprise alternating net positively charge layers such as poly (allylamine hydrochloride), or PAH, layers 30*a*, 30*b* and negatively charged layers such as poly(styrene sulfonate), or PSS, layers 32*a*, 32*b*.

PEMs 28 are created by exposing the surfaces of the microchannel 14 to alternating solutions of positively and negatively charged polyelectrolytes. The layers are adsorbed onto the substrate 12 or previous layer by non-covalent interactions resulting in multilayers having multiple electrostatic bonds that are stable and uniform.

Although PEMs 28 are depicted as comprising four PEMs, (i.e., two PAH layers 30*a*, 30*b* and two PSS layers 32*a*, 32*b*), PEMs 28 may vary in the number of polyelectrolyte layers. For example, PEMs 28 may comprise as few as a single layer (e.g., either a single PAH layer 30*a* or a single PSS layer 32*a*). Alternatively, PEMs 28 may comprise 15 or more layers of alternating net positively and net negatively charged layers until a desired number of layers are formed. Preferably, PEMs 28 contain a sufficient number of layers such that selected surfaces of microchannel 14 (i.e., the outermost PEM layer) will have a desired, uniform charge. What should become obvious to one of ordinary skill is that, in this case where the substrate is negative, an odd number of layers results in a positively charged top (i.e., outermost) layer corresponding to a PAH layer 30, while channels with an even number of layers have a net negatively charged PSS layer 32. In the case where the substrate is positive, an odd number of layers results in a negatively charged top layer while channels with an even number have a net positively charged layer.

Formation of PEMs 28 is provided by deposition of polyelectrolytic layers using a method that may include first treating the substrate 12 with a 1 M NaOH solution at 55° C. for 15 minutes. This pre-treatment step is not necessary for all materials. Next, the substrate 12 was rinsed with 18MΩ·cm deionized water and dried with nitrogen. A 20 mM PAH solution in a 0.5 M NaCl and having a pH 9, was introduced into the microchannel 14 and completely covered the microchannel surfaces 16, 18 and 20. The first PAH solution was allowed to stand for 30 minutes. The PAH solution was first removed from the microchannel 14 by rinsing thoroughly with water and the microchannel 14 was subsequently dried. During the 30 minute period, PAH molecules adsorb onto the surfaces 16, 18, and 20 surface, thereby forming the first PAH layer 30*a*. Alternatively, this coating procedure may be performed in an enclosed channel where the lid is simultaneously derivatized.

Next, an aqueous 60 mM PSS solution in 0.5 M NaCl, pH 9, was introduced into the microchannel 14, completely covering the microchannel 14. The PSS solution was allowed to stand for 30 minutes allowing PSS molecules to adsorb onto the previously deposited PAH layer 30*a* thereby forming the first PSS layer 32*a*. The PSS solution was rinsed off with water and the microchannel 14 was dried. Alternating layers of PAH layer 30*b* and PSS layer 32*b* were deposited by applying the appropriate solution for 5 minutes followed by a exhaustive water rinses in between each solution application.

Although PEMs 28 are depicted as having only four layers, the process of applying alternate layers of PAH and PSS can continue further until a desired number of layers are deposited. In this instance, as a result, microchannels with an odd number of layers will have a positively charged top layers corresponding to a PAH layer 30 while those with an even number of layers will have a negatively charged PSS layer 32 as its outermost layer.

Figure 1C:
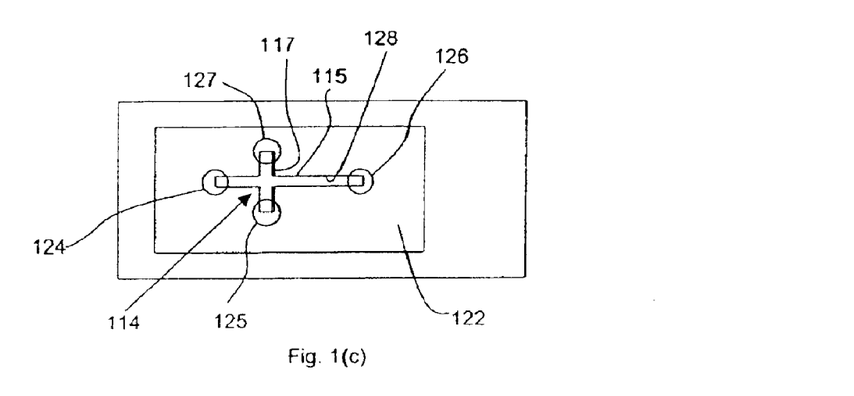
FIG. 1(c) is a top view of a microfluidic device having a cross-shaped microchannel design according to the present invention.

Referring now to FIG. 1(*c*), in one specific embodiment, a microchannel 114 comprises subchannels 115 and 117. A lid 122 is disposed over the microchannel 114 and may include four holes 124, 125, 126 and 127 which serve as fluid reservoirs for the microchannel 114. PEMs 128 are applied to the surfaces of subchannels 115, 117 in a manner similar to the deposition of PEMs 28 described above. The lid 122 may or may not be treated but if untreated, lid 22 retains its native charge. The PEMs 28, 128 provide a means for controlling the flow direction, rate of flow of a fluid, and the electroosmotic mobility (EOF) in the microchannels 14, 114. Further, the PEMs 28, 128 produces microchannels 14, 114 with excellent wetability, thereby allowing facile filling of the microchannels 14, 114. Also, the deposition of PEMs can be used to improve biocompatibility.

As described above, the EOF of the microchannels 14, 114 is affected by outermost surfaces of the microchannel 14, 114. Further, the flow direction in the microchannel 14, 114 may be altered depending upon the charge of the outermost surface. When an electric current is applied to opposing ends of a microchannel with a negative top layer, in this case PSS, the flow of a solution such as 10 mM phosphate buffer, pH 7 is from anode to cathode in the microchannel. Conversely, the flow in microchannels with a positively charged top layer, in this case PAH, was reversed and the solution flowed from the cathode to the anode and was designated as a negative flow. What should be apparent to one of ordinary skill is that other polyelectrolytes can be employed other than PAH and PSS, and the direction and magnitude of fluid flow in the microchannel will depend on the pK of the polyelectrolyte and the pH of the solution. It should also be apparent that with a positively charged substrate, the deposition order of the layer is reversed.

TABLE 1

| Substrate | EOF Mobility |
| --- | --- |
| PETG | $4.3 \pm 0.4 \times 10^{-4}$ |
| PC | $3.0 \pm 0.3 \times 10^{-4}$ |
| PS | $2.5 \pm 0.4 \times 10^{-4}$ |
| PMMA | $1.3 \pm 0.4 \times 10^{-4}$ |

Table 1 summarizes the EOF mobility ($cm^2/V \cdot s$) of microchannels formed in various substrate plastics with polydimethyl siloxane (PDMS) lids.

TABLE 2

| Surface Treatment | PETG/PDMS | PS/PDMS |
|---|---|---|
| 1 M NaOH | $5 \pm 1 \times 10^{-4}$ | |
| 3 Layer PEM | $-1.8 \pm 0.3 \times 10^{-4}$ | |
| 4 Layer PEM | $4.2 \pm 0.2 \times 10^{-4}$ | |
| 13 Layer PEM | $-1.7 \pm 0.3 \times 10^{-4}$ | $-1.3 \pm 0.2 \times 10^{-4}$ |
| 14 Layer PEM | $4.8 \pm 0.5 \times 10^{-4}$ | $4.1 \pm 0.2 \times 10^{-4}$ |

Table 2 summarizes the EOF mobility (cm$^2$/V·S) of various non-limiting illustrative examples of PEM derivatized microchannels made in substrates of PETG or PS with PDMS lids. From Tables 1 and 2, as will become clear to one of ordinary skill, PEMs composed of 13 or 14 layers results in microchannels with similar mobilities in PETG and PS substrates despite differences in mobility of their respective, native plastics. Consequently, the present method of surface derivatization with PEMs can produce similar surfaces on different plastic materials thereby allowing flexibility in substrate polymer selection for a given or desired application.

EOF mobility is also affected by the native negative surface charge of the lids when the lid is not derivatized 22, 122. For example, the net flow rate is slower in microchannels formed in either PETG or PS substrates with PEMs having a positive PAH layer 30 as its top or outermost layer using either PETG or PS substrates with an uncoated PDMS lid. Conversely, in negatively charged microchannels (i.e., microchannels with a negatively charged top or outermost layer), there is an increase in net flow due to the native negative charge on the PDMS lids 22, 122. Therefore, the native negative charge of the PDMS lid increases the net flow in the microchannels with the negatively charged PSS top or outermost layer, and decrease the net flow in microchannels with the positively charged PAH layer.

One significant practical advantage of the PEM coated microchannels is the ease with which the microchannels may be filled with a liquid as compared with untreated plastics. The hydrophilic character of the PEMs facilitates wetting of the microchannel surfaces.

Further, unlike using uncoated (i.e., native) plastic substrates the PEMs coated microchannels of the present invention do not require priming and associated problems therewith. Using the PEM coated microchannels, priming may not be necessary and air bubbles do not get pinned to the walls on the PEM coated microchannel surfaces during filling. Consequently, there is a reduction in time required to prepare the microchannels for use and may facilitate the use of plastic microchannels for a wider variety of applications.

A further advantage of PEM coated channels is the ability to regenerate the outermost layer after use or exposure by flowing the final polyelectrolyte solution through the microchannel. For example, if PSS layer 32, 132 is the top, outermost layer of microchannel 14, 114, a solution comprising PSS can be re-applied to microchannels 14, 114. The PSS is allowed to adsorb to the microchannel surfaces thereby regenerating the top layer.

In one specific, further embodiment, various molecules are immobilized in or on the PEMs. The molecules may include, but are not limited to proteins, antibodies and DNA. These molecules may be immobilized in the PEMs by adding the molecules to the desired PAH and PSS solutions during PAH and PSS layer deposition. Alternatively, or in addition, the desired molecules could be introduced into a derivatized microchannel, i.e. after PEMs deposition is complete. Even if the desired molecules are introduced to the outermost surface of the PEMs, the molecules may diffuse from the outermost layer to one or more inner layers.

Furthermore, the PEMs layers may be used to provide biocompatible microchannels by decreasing the adsorption of biological species.

Figure 2A:
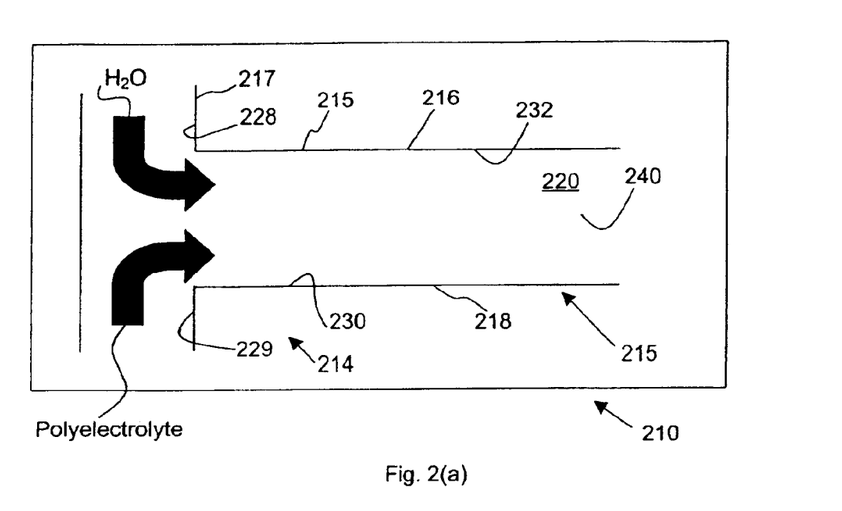
FIG. 2(a) is a top view depicting laminar flow in a microfluidic device having a "T"-shaped microchannel design used to selectively deposit polyelectrolyte layers in a single half of the microchannel.
Figures 2B, 2C:
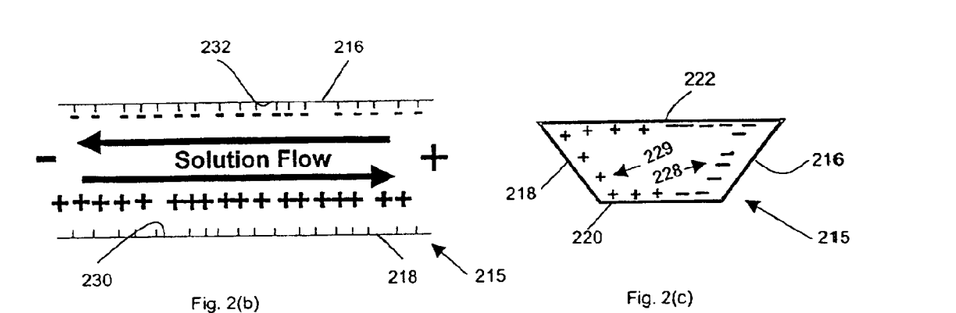
FIG. 2(b) is a top view of the microfluidic device depicted in FIG. 2(a)
FIG. 2(c) is a cross-sectional view of the microchannel depicted in FIG. 2(a)

Further illustration of the use of PEMs to control or alter EOF is provided in reference to a microfluidic device 210 depicted in FIGS. 2(a)–2(c). As described above, since the direction of the EOF is determined by the charge on a substrate surface, selective deposition of PEMs on various selected surfaces of microchannel 214 along with the application of a controlled voltage can be used to direct the flow in microfluidic devices such as microfluidic device 210.

Microchannel 214 comprises a subchannel 215 in which a portion of the channel surface 216 has PEMs 228, 232 with a top or outermost layer comprising a PSS layer 232 and a different portion of the channel surface 218 has PEMs 229 with outermost surface comprising a PAH layer 229, 230. The surfaces of subchannel 215 were treated by exposing the microchannel 214 to alternating solutions of positively and negatively charged polyelectrolytes to form the desired PEMs, as described above with reference to microchannels 14, 114. The substrate 215 may be composed of a variety of polymeric materials including but not limited to polystyrene or PMMA. The microchannel 214 may be covered with a lid (not shown). Laminar flow patterning is used to fill one half of the microchannel 214 with a positively charged PAH solution and the other half with water as depicted in FIG. 2(a). Further details on the laminar flow patterning may be made by reference to Kenis, P. K., et al., Science 1999, 285, 83, herein incorporated by reference.

As a result, one half of the microchannel 214 comprises a positively charged PAH layer 230 as the outermost surface of PEMs 229 as shown in FIG. 2(c). The other half of the microchannel 214 is oppositely charged comprising negatively charged PSS layer 232 on outermost surface of PEMs 228 as shown in FIG. 2(c). The division of the microchannel 214 into two oppositely charged halves is indicated by a dotted line 240.

While FIGS. 2(a)–2(c) depict coating a microchannel 214 by selectively depositing a positive PAH layer over one half of the microchannel 214 surfaces, it should be readily apparent to one of ordinary skill that selective deposition of a negatively charged PSS layer may be formed over selected microchannel surfaces comprising a previously deposited positively charge layer.

The derivatized microchannel 214 results in a bi-directional electroosmotic flow within a single subchannel 215 (FIG. 2(b)). Specifically, the flow of a fluid on the PSS derivatized side (i.e., microchannel surfaces with outermost surface 232 disposed thereon) moved from anode to cathode indicating positive velocities while flow in the PAH derivatized side (i.e., microchannel surfaces with outermost surface 230 disposed thereon) was from cathode to anode indicating negative velocities. Thus, side-by-side bi-directional flow is provided in a single microchannel as described in detail in Barker et al. Anal. Chem. 2000.

In an alternative embodiment, opposite electroosmotic flow directions in the same microchannel may be achieved using a positively derivatized microchannel with a negatively charged lid thereby achieving top-bottom opposite flows.

Figure 3A:
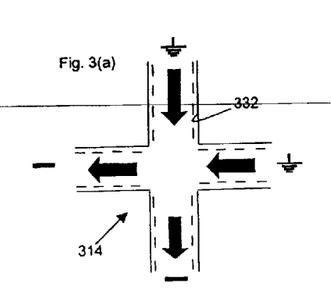
FIGS. 3(a)–3(e) are top views of various cross-shaped microchannels schematically depicting fluid flow therein.
Figure 3B:
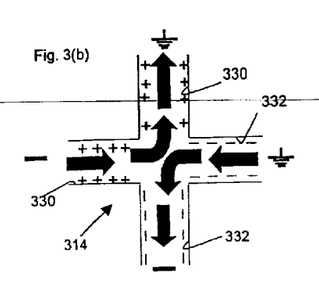
Figure 3C:
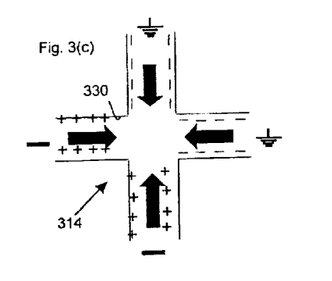
Figure 3D:
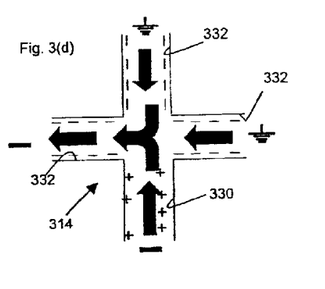
Figure 3E:
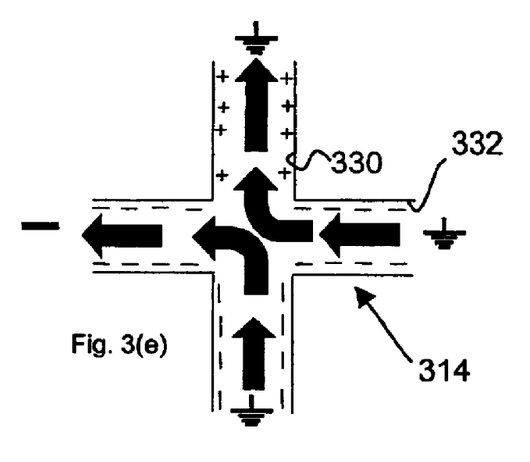

Complex flow patterns within a microchannel is next described with reference to FIGS. 3(a)–2(e). FIGS. 3(a)–3(e) depict five microchannels, each formed of two subchannels which form a cross-shaped design consisting of four arms. PEMs are formed on the surfaces of the microchannels 314. The various arms have PEM derivatived surfaces with either a positively or negatively charged outermost layer as desired.

The cross designs were treated to have different charges on the various arms by treating the entire microchannel 314 first with a desired number of PEMs as previously described above with reference to microfluidic device 10. Next, the desired charged polymer solution was applied into the selected arms. Care was taken such that the solution only entered the desired arm during the derivatization and rinsing processes.

The flow of fluid through the various microfluidic devices depicted in FIGS. 3(a)–3(e) are indicated by the arrows. Voltage was applied to various arms of the microfluidic device as indicated. The bulk flow in the microchannels with a negatively charged PSS top layer (the outermost layer of the PEMs) was from anode to cathode while the bulk flow in microchannels with a positively charged PAH top layer was reversed and flowed from cathode to anode. Flow in the devices could be controlled by either grounding or applying a voltage to each of the individual arms.

FIGS. 3(a)–3(e) diagram flow patterns achieved in five devices with different charges on various, selected microchannel surfaces but with the same applied voltages. As will become obvious to one of ordinary skill in the art, the use of oppositely charged channels simplifies the applied voltages needed to produce various complicated flow patterns.

Although the invention has been described above in relation to preferred embodiments thereof, it will be understood by those skilled in the art that variations and modifications can be effected in these preferred embodiments without departing from the scope and spirit of the invention.

What is claimed is:

1. A microchannel device, comprising:
   a plastic substrate having a microchannel formed therein, said microchannel having a geometry with at least one spatial dimension on the order of micrometers and a longitudinal axis;
   polyelectrolyte layers comprising alternating layers of at least one net positively charged layer and at least one net negatively charged layer, said polyelectrolyte layers disposed along at least a portion of a microchannel surface; and
   a lid disposed over said microchannel and having a lid surface facing said microchannel.

2. The microchannel device of claim 1, wherein said plastic is selected from the group consisting of polystyrene, poly(ethylene terephthalate glycol), poly(methyl methacrylate), and polycarbonate.

3. The microchannel device of claim 1, wherein said net negative charged layer comprises poly(styrene sulfonate).

4. The microchannel device of claim 1, wherein said net positive charged layer comprises poly(allylamine hydrochloride).

5. The microchannel device of claim 1, wherein said lid is formed of one of an elastomeric polymer, a hard plastic and a laminating film.

6. The microchannel device of claim 1, wherein further polyelectrolyte layers are disposed on said lid surface.

7. The microchannel device of claim 1, wherein an outermost layer of said polyelectrolyte layers is a negatively charged layer.

8. The microchannel device of claim 1, wherein an outermost layer of said polyelectrolyte layers is a positively charged layer.

9. The microchannel device of claim 1, wherein an outermost layer of said polyelectrolyte layers disposed on a first longitudinally extending portion of said microchannel surface is negatively charged and an outermost layer of said polyelectrolyte layers disposed on a second adjacent longitudinally extending portion of said microchannel surface is positively charged.

10. The microchannel device of claim 9, wherein an outermost layer of said polyelectrolyte layers disposed on said lid surface comprises a negatively charged longitudinally extending portion adjacent to said first portion of said microchannel surface and a positively charged longitudinally extending portion adjacent to the second portion of said microchannel surface.

11. The microchannel device of claim 1, wherein said microchannel comprises at least two intersecting subchannels defining at least three arms, each of said arms having disposed along at least a portion thereof alternating polyelectrolyte layers comprising at least one net positively charged layer and at least one net negatively charged layer.

12. The microchannel device of claim 11, wherein said at least two subchannels form a "T"-shaped pattern consisting of three arms.

13. The microchannel device of claim 11, wherein said at least two subchannels form a cross-shaped consisting of four arms.

14. The microchannel device of claim 11, wherein an outermost layer of said polyelectrolyte layers disposed on at least one arm has a first charge and an outermost layer of said polyelectrolyte layers disposed on at least one further arm has a second, opposite charge.

15. The microchannel device of claim 11, wherein an outermost layer of said polyelectrolyte layers disposed on a first longitudinally extending part of one said arm is negatively charged and an outermost layer of said polyelectrolyte layers disposed on a second adjacent longitudinally extending part of said one arm is positively charged.

16. The microchannel device of claim 11, wherein an outermost layer of said polyelectrolyte layers disposed on a bottom surface of at least one arm of said at least three arms comprises a longitudinally extending negatively charged portion and an adjacent longitudinally extending positively charged portion.

17. The microchannel device of claim 1, further comprising one of the group consisting of proteins, antibodies, and DNA disposed on an outermost layer of said polyelectrolytic layers.

18. The microchannel device of claim 1, further comprising one of the group consisting of proteins, antibodies, and DNA disposed within selected layers of said polyelectrolyte layers.

19. The microchannel device of claim 1, wherein said microchannel has a cross sectional geometry selected from the group consisting of trapezoidal, semicircular, rectangular, and square.

20. A method of manufacturing a microchannel device, said method comprising the steps of:
   providing a plastic substrate with a microchannel formed therein, the microchannel having at least one spatial dimension on the order of micrometers and a longitudinal axis;
   exposing selected surfaces of the microchannel to a first solution comprising positively charged polyelectrolytes;
   exposing the selected surfaces of the microchannel to a second solution comprising negatively charged polyelectrolytes; and repeating said steps of exposing the selected surfaces of the microchannel to the first solution and said exposing the selected surfaces of the microchannel to the second solution, alternately, as necessary, to form a desired number of polyelectrolyte multilayers on the selected surfaces.

21. The method of claim 20, wherein said steps of exposing the selected surface produces a positively charged microchannel.

22. The method of claim 20, wherein the negatively charged polyelectrolytes comprise poly(styrene sulfonate).

23. The method of claim 20, wherein the positively charged polyelectrolytes comprise poly(allylamine hydrocholide).

24. The method of claim 20, wherein said steps of exposing the surfaces of the microchannel to the first solution and exposing the surfaces of the second solution comprises filling the microchannel with the respective solution and allowing the respective polyelectrolyte to adsorb to the selected surfaces or previous layer of the microchannel.

25. The method of claim 20, wherein said step of providing a substrate further comprises providing a lid over the microchannel, the lid having a lid surface facing the microchannel.

26. The method of claim 20, wherein the lid surface has a charge opposite a charge on an outmost layer of the polyelectrolytic multilayers.

27. The method of claim 20, wherein the lid is placed over the channel prior to PEM deposition and the lid is derivatized in a similar manner as the selected surfaces of the microchannel.

28. The method of claim 20, further comprising the step of selectively depositing a charged layer on a selected first microchannel surface having a charge opposite a charge on an outermost layer disposed on a selected second microchannel surface.

29. The method of claim 28, wherein said step of selectively depositing a charged layer comprises:
using a laminar flow patterning to fill one half of the microchannel with a selected polyelectrolyte solution having a charge opposite a charge of an outermost layer of the polyelectrolyte multilayers and to fill the other half of the microchannel with a solution that does not contain the selected polyelectrolyte.

30. The method of claim 20, wherein the microchannel is formed from two intersecting subchannels thereby defining at least three arms.

31. The method of claim 30, wherein the selected surfaces are surfaces of one of the arms.

32. The method of claim 30, further comprising selectively exposing the surfaces of at least one said arm to a desired charged polyelectrolyte solution having a charge opposite a charge of an outermost layer of the polyelectrolyte layers on the surfaces of at least one remaining arm.

33. The method of claim 20, further comprising the step of re-generating an outermost layer of the polyelectrolyte multilayers by re-exposing the selected surfaces to the polyelectrolyte solution last applied.

34. The method of claim 20, further comprising the step of immobilizing selected molecules to an outermost layer of the polyelectrolyte multilayers.

35. The method of claim 34, wherein the molecules are selected from the group consisting of proteins, antibodies and DNA.

36. The method of claim 35, wherein said step of immobilizing the selected molecules comprises adding the selected molecules to at least one of the first solution and second solution.

37. A microchannel device, comprising:
a plastic substrate having a microchannel formed therein, said microchannel comprising, a first longitudinally extending portion having an outermost surface and a second adjacent longitudinally extending portion having an outermost surface;
a first polyelectrolyte layer disposed on the outermost surface of said first portion and a second polyelectrolyte layer disposed on the outermost surface of said second portion, said first polyelectrolyte layer and said second polyelectrolyte layer having opposite charges; and
a lid disposed over said microchannel and having a lid surface facing said microchannel.

38. The microchannel device of claim 37 wherein said first polyelectrolyte layer comprises an outermost layer of a first polyelectrolyte multilayer disposed on said first portion.

39. The microchannel device of claim 37 wherein said second polyelectrolyte layer comprises an outermost layer of a second polyelectrolyte multilayer disposed on said second portion.

40. The microchannel device of claim 37, wherein said plastic substrate comprises a plastic selected from the group consisting of polystyrene, poly(ethylene terephthalate glycol), poly(methyl methacrylate), and polycarbonate.

41. The microchannel device of claim 37, wherein said first polyelectrolyte layer comprises poly(allylamine hydrochloride).

42. The microchannel device of claim 37, wherein said second polyelectrolyte layer comprises poly(styrene sulfonate).

* * * * *